United States Patent
Bousque et al.

(10) Patent No.: US 9,596,859 B2
(45) Date of Patent: Mar. 21, 2017

(54) EMULSIFIABLE CONCENTRATE FOR A PHYTOSANITARY COMPOSITION, PHYTOSANITARY COMPOSITION AND PHYTOSANITARY FILM

(75) Inventors: Mélanie Bousque, Higueres Souye (FR); Maurice Bourrel, Pau (FR); Christian Laemmer, Croisy sur Seine (FR); Jean-Philippe Gingras, Pau (FR)

(73) Assignee: Total Marketing Services, Puteaux (FR)

( * ) Notice: Subject to any disclaimer, the term of this patent is extended or adjusted under 35 U.S.C. 154(b) by 229 days.

(21) Appl. No.: 13/514,212

(22) PCT Filed: Dec. 7, 2010

(86) PCT No.: PCT/IB2010/055623
§ 371 (c)(1),
(2), (4) Date: Jun. 6, 2012

(87) PCT Pub. No.: WO2011/070503
PCT Pub. Date: Jun. 16, 2011

(65) Prior Publication Data
US 2012/0245232 A1    Sep. 27, 2012

(30) Foreign Application Priority Data
Dec. 7, 2009  (FR) ..................... 09 58704

(51) Int. Cl.
*A01N 61/02*    (2006.01)
(52) U.S. Cl.
CPC ................... *A01N 61/02* (2013.01)
(58) Field of Classification Search
None
See application file for complete search history.

(56) References Cited

U.S. PATENT DOCUMENTS

| 5,178,871 | A | * | 1/1993 | Thill ..................... A01N 25/04 424/405 |
| 5,906,727 | A | * | 5/1999 | Wittenbrink ........... C10G 45/58 208/14 |
| 6,515,031 | B2 | | 2/2003 | Fefer |
| 6,673,360 | B2 | | 1/2004 | Fefer |
| 2008/0194704 | A1 | * | 8/2008 | Bhatnagar et al. ........... 514/762 |
| 2010/0016447 | A1 | | 1/2010 | Fefer |
| 2012/0010109 | A1 | | 1/2012 | Westelynck et al. |

FOREIGN PATENT DOCUMENTS

EP    0 392 127    10/1990

OTHER PUBLICATIONS

ASTM D396—fuel oil properties (1986) [downloaded from the internet on Jan. 28, 2014 from http://www.bunkering.co.kr/table/dtls-fuel.htm].*
Purespray Foliar 15E Label (2008) [downloaded from the internet on Jan. 29, 2014 from http://pdf.tirmsdev.com/Web/207/30480/207_30480_LABEL_English_.pdf?download=true].*
Sorbitan monooleate techsheet 2010 [downloaded on Dec. 18, 2014 from the archived website https://web.archive.org/web/20100411115804/http://chemicalland21.com/lifescience/foco/SORBITAN%20OLEATE.htm].*

* cited by examiner

*Primary Examiner* — Sue Liu
*Assistant Examiner* — Thor Nielsen
(74) *Attorney, Agent, or Firm* — Harness, Dickey & Pierce, P.L.C.

(57) ABSTRACT

An emulsifiable concentrate for emulsified phytosanitary composition, including more than 90% by weight of at least one mixture of hydrocarbons having a distillation cut greater than 250° C., less than 20% by weight of n-paraffins and less than 1% aromatics, and from 1 to 4% by weight of a mixture of at least two surfactants TA1 and TA2, such that TA2 is more hydrophobic than TA1, the HLB of the mixture of which varies from 6 to 10.

19 Claims, No Drawings

EMULSIFIABLE CONCENTRATE FOR A PHYTOSANITARY COMPOSITION, PHYTOSANITARY COMPOSITION AND PHYTOSANITARY FILM

CROSS-REFERENCE TO RELATED APPLICATIONS

This application is a National Phase Entry of International Application No. PCT/IB2010/055623, filed on Dec. 7, 2010, which claims priority to French Patent Application Ser. No. 09 58 704, filed on Dec. 7, 2009, both of which are incorporated by reference herein.

BACKGROUND AND SUMMARY

The present invention relates to an emulsifiable concentrate for a phytosanitary composition, emulsified in water, intended for spraying onto crops, in particular the leaves and trunks of fruit trees for the purposes of protection, in particular from insects, but also for their fungistatic properties preventing the development of diseases. It also relates to the emulsified phytosanitary composition, its method of production, its use, but also the protective film deposited onto the plants.

It is known to use phytosanitary compositions to improve crop protection, these compositions being capable of fulfilling the role of fungicide or also insecticide. They are generally sprayed onto crops in the form of water/oil emulsions in the presence of surfactant additives.

The use of oils of petroleum origin emulsified in water and sprayed onto crops as an insecticide is long-established. Suitably prepared, such oils are generally less phytotoxic than many synthetic pesticides, and make it possible to target acarids, flies, scale insects, chinch bugs, aphids and other crawling or flying insects while having only a moderate effect on the development of trees, plants and crops in general. However, the type of oil and the type of surfactant additive must be non-toxic to plants. Most of the surfactants used are harmful to the environment and toxic to aquatic organisms. The manufacturer will choose from the conventional refined oils obtained from crude oil and/or distillates originating from refining by solvent extraction or by hydrotreatment of base oils, those which will be the least toxic but most effective for example against insect and/or fungal attack. Thus it has been noted that the higher the paraffin content of the oil produced, i.e. comprising compounds having a linear or branched saturated carbon chain, the more effective it is against insects and the less phytotoxic to plants. However, the pour point of such oils having a high concentration of normal paraffins is higher, making their application more difficult in temperate countries, in particular for treatments carried out in winter, as the concentrate obtained from this oil congeals.

In their final formulation, such water/oil emulsions generally comprise from 1 to 3% by weight of an emulsifier with respect to the quantity of hydrocarbons in order to ensure the stability of the emulsion throughout crop spraying. Conventional emulsifiers include the ethoxylated alkylphenols, but also combinations of additives as described in U.S. Pat. Nos. 6,673,360 and 6,615,031. These patents suggest combining polyethoxylated alcohols comprising $C_{10}$-$C_{16}$ carbon chains, the average number of ethoxylated groups per carbon chain being 2.8, in a mixture with glycerol mono/dioleates. They recommend the use of hydrocracked and/or hydroisomerized oils, comprising more than 99% saturated compounds, these combinations of additives making it equally possible to incorporate soft water or hard water, i.e. having a high salt content, into these emulsions.

The purpose of the present invention is to make available emulsifiable concentrates that are stable during storage, easily form an emulsion, but which break on contact with the plant to form the homogenous oil film over the crops, in particular the trunks, branches and leaves, in order to perform an insecticide function, and from which the water is instantly removed by runoff. This dual requirement for stability before and during spraying and immediate separation afterwards is central to the invention. Moreover, the surfactant system must be harmless to the environment. Moreover, a further purpose of the present invention is to obtain stable emulsifiable concentrates that can easily be transported, avoiding unnecessarily transporting quantities of water since it is available on site, and the emulsifying of which is facilitated at the site of the crops to be treated. A further purpose of the invention is that, when the emulsion breaks on contact with the plants and bushes, the quantity of water remaining in the deposited protective film is minimal.

The subject of the present invention is thus an emulsifiable concentrate for an emulsified phytosanitary composition, comprising more than 90% by weight of at least one mixture of hydrocarbons having a distillation cut greater than 250° C., comprising less than 20% by weight n-paraffins and less than 1% aromatics, and from 1 to 4% by weight of a mixture of at least two surfactants TA1 and TA2, such that TA2 is more hydrophobic than TA1, the HLB of the mixture of which varies from 6 to 10. Once sprayed on the trees and the leaves, the emulsified compositions of these concentrates form a film which will act as an insecticide, or also a fungicide: the application of these compositions may thus help to cure diseases or may also protect crops from potential diseases caused by the presence of harmful insects and/or to the occurrence of fungal species which are unfavorable to their development. These concentrates are harmless both to the environment and to humans. Moreover, these compositions deposited as a film do not block photosynthesis by the plants although the film slows their growth. This drawback can advantageously be mitigated by planning the spraying periods according to the desired speed of growth and the detrimental effect of the surrounding environment with respect to crop growth. The film deposit is primarily a physical treatment: the insecticidal effect is obtained by asphyxia of the insects present (lack of air) or as a barrier limiting access.

Within the framework of the present invention, the concentrate (in the form of an emulsion) advantageously comprises from 0.0001% to 1% by weight of water in order to avoid the appearance of a deposit corresponding to precipitation of TA1. Moreover, preferably a mixture of surfactants will be chosen, the HLB difference between TA1 and TA2 of which varies from 3 to 11 and the HLB of the mixture of which is comprised between 6 and 10.

Among the hydrocarbons originating from refining, mixtures are preferred that comprise less than 10 ppm sulphur and less than 100 ppm aromatics, and among these the hydrodewaxed hydrocarbons containing more than 50% by weight isoparaffins and desulphurized and dearomatized hydrocarbons containing more than 20% by weight naphthenes. By naphthenes is also meant di- and tricyclic naphthenes. The advantage of these hydrocarbons is that unlike normal paraffins, their pour point determined by the ASTM D97 is substantially lower than that of the normal paraffins or n-paraffins and can be well below −10° C., which facilitates their transport and their storage in cold environments.

More particularly, the hydrocarbons containing more than 60% isoparaffins originating from isodewaxing processes, having a distillation cut comprised between 300 and 400° C., the pour point of which is below −10° C. are preferred. Among these non-phytotoxic hydrocarbons, hydrocarbon mixtures comprising more than 50% by weight of hydrocarbons containing from 15 to 30 carbon atoms are preferred, and preferably more than 70% of hydrocarbons containing from 18 to 26 carbon atoms. Other hydrocarbons can be used, these are gas oil cuts having boiling points above 250° C., originating from hydrocracking vacuum distillate gas oils or other refining processes, these cuts having been desulphurized and/or dearomatized by catalytic hydrogenation then distilled into cuts with ranges of less than 75° C. The preferred cuts, of temperatures varying from 300 to 400° C., comprising more than 20% naphthenes, have the advantage of achieving pour points below −15° C. The concentrate according to the invention will preferably comprise from 2 to 3% surfactant TA1 and from 0.1 to 0.9% surfactant TA2. In order to obtain the optimum stability of the concentrate, its water content must be maintained between 0.05 and 0.5% by weight of the concentrate.

Among the surfactants available on the market, TA1 is chosen from the carboxylic acids, optionally polyalkoxylated, comprising a carbon chain with from 16 to 20 carbon atoms having at least one olefin bond, each polyalkoxylated group comprising from 3 to 15 alkoxyl radicals, itself comprising 1 to 4 carbons per oxygen atom. The HLB of this surfactant will preferably vary between 5 and 16, and preferably from 8 to 12. In a preferred embodiment of the invention, the surfactant TA1 is a polyethoxylated oleic acid comprising from 4 to 8 ethoxylated radicals, preferably 6 ethoxylated radicals on average. The surfactant TA2 is chosen from sorbitan mono- and/or polycarboxylates, polyethoxylated sorbitan mono- and/or polycarboxylates, glycerol mono and/or polycarboxylates or polyethoxylated sorbitan mono- and/or polycarboxylates, wherein the polycarboxylate groups comprise 1 to 3 carbon chains of 12 to 20 carbon atoms having at least one olefin bond, and each polyethoxylated group comprises 1 to 5 ethoxylated groups. The HLB of the surfactant TA2 varies from 1 to 11 and preferably from 1 to 5. Sorbitan monooleate and glycerol monooleate and their mixture are preferred.

A further subject of the invention is the emulsion comprising from 0.5 to 10% by weight of the concentrate as described above and from 99.5 to 90% fresh and/or salt water. Preferably the mixture is emulsified (or macro-emulsified) such that the size of the oil droplets are not too large to allow a minimum stability of the emulsion for sufficient time for spraying onto the crops, but not too small to allow the emulsion to break on the leaf and for the water to run off. These conditions correspond to creaming time or destabilization time of the emulsion measured in the laboratory by the CIPAC (Collaborative International Pesticides Analytical Council) MT36 method. In order to obtain optimum stability of the emulsion, a creaming time of less than 10 minutes is preferred, preferably comprised between 25 seconds and 2 minutes. Preferably, the emulsion comprises from 0.5 to 3% by weight of the concentrate and from 97 to 99.5% fresh and/or salt water.

A further subject of the invention is the method of preparing the emulsion at the crop treatment site. Once transported to the spraying site, the concentrate will be mixed in a tank with the necessary quantity of water. The resulting mixture will be emulsified by means of a static emulsifier or a rotor-stator mixer placed inside the tank or on a by-pass pipe external to the tank allowing recirculation of the emulsion and its homogenization.

A further subject of the invention is use of the emulsion for insecticidal and/or fungicidal crop treatment in which the crops may be of any kind. The emulsion is particularly suitable for fruit tree growing, in particular banana and citrus fruit growing (orange, lemon trees, etc.). A final subject of the invention is the homogenous oil film deposited on the crops, in particular on the trunks and leaves, comprising less than 5% water, preferably less than 0.5%. The surfactants TA1 and TA2 are entrained with the water.

DETAILED DESCRIPTION

The following examples are given for the purposes of illustration, but cannot be considered as limiting the invention.

Example 1

The present example is intended to describe the preparation of emulsifiable concentrates that are composed of 3% by weight of a mixture of two surfactants TA1 and TA2, 0.1% by weight of water and of 96.9% by weight of hydrocarbons. These hydrocarbons are constituted by a dearomatized gas oil cut, the temperature of the cut being comprised between 305 and 380° C. containing 27% naphthenes and 73% paraffins, of which more than 90% by weight are isoparaffins.

Several combinations of surfactants TA1 and TA2 were tested: the characteristics of these mixtures are described in Table I below. The samples of concentrates obtained are referenced Xi.

TABLE I

| | Surfactants | | HLB eq | | | Ecotoxicity | | Visible |
|---|---|---|---|---|---|---|---|---|
| Concentrates | TA1 | TA2 | TA1 | TA2 | Mix | TA1 | TA2 | deposit |
| X1 | 2 OE Ethoxylated C13-C15 alcohol | Sorbitan monooleate | 5.9 | 4.3 | 5.6 | High | Low | No |
| X2 | 20 OE Ethoxylated Triglycerides of rapeseed | Sorbitan monooleate | 8.9 | 4.3 | 7.1 | Low | Low | No |
| X3 | 10 OE Ethoxylated oleic acid | Sorbitan monooleate | 12.0 | 4.3 | 9.4 | Low | Low | No |
| X4 | 6 OE Ethoxylated oleic acid | Sorbitan monooleate | 9.8 | 4.3 | 8.9 | Low | Low | No |

The mixture satisfies a linear mixture law on the basis of the weight fractions of each of the surfactants: thus the average HLB is equal to xHLB(TA1)+yHLB(TA2), x and y corresponding to the weight concentrations of these TAi in the mixture.

The emulsions according to the invention, prepared from concentrates Xi, satisfy certain characteristics. They do not show a deposit after storage for 14 days at 54° C. according to the procedure recommended by CIPAC MT 46.3.1, and they satisfy the creaming test described below. The creaming test is carried out according to the CIPAC MT 36 procedure. The emulsions are prepared in a graduated test tube by dispersing 5 mL of an emulsifiable concentrate in 95 mL of hard water (containing 274 ppm $CaCO_3$ and 27 ppm MgO). The concentrate and the water are preheated to 30° C. in order to emulsify more easily, and the emulsion is formed by successively upturning the same test tube after it has been sealed. For each test tube, the creaming time is then measured, i.e. the time required to obtain 4 mL hydrocarbons. Table II shows the creaming time for each of the concentrates Xi of Table I.

TABLE II

| Emulsion | concentrate | HLB eq | Creaming time/4 mL oil (seconds) |
|---|---|---|---|
| E1 | X1 | 5.6 | 33 |
| E2 | X2 | 7.1 | 15 |
| E3 | X3 | 9.4 | 17 |
| E4 | X6 | 8.9 | 40 |

If the stability of the emulsions according to the invention is compared to that of the emulsions of the prior art (here E1), it is noted that the emulsions according to the invention give a reasonable creaming time, i.e. a sufficient resistance to separation before spraying and water run-off on contact with the crops. It is noted moreover, that the presence of a deposit is prohibitive for a food quality application onto citrus fruit. In fact, the appearance of a deposit is evidence of a homogeneity deficiency of the emulsion and therefore of a product having properties that are different from those expected.

Moreover, the concentrates of additives of the emulsions according to the invention, X2, X3 and X4 present the best average HLB compromise with surfactants having very different HLB values. Unlike the emulsions of the prior art, these surfactants are all ecotox.

Example III

The present example aims to exemplify the fungicidal and insecticidal effects of the emulsion according to the invention. Samples of products to be tested on citrus groves (oranges) are prepared. The reference R corresponds to an untreated citrus plot.

Emulsions according to the invention are used, obtained from X6, at 3% in a mixture of hydrocarbons as described in Example 1 for forming the concentrate. This concentrate is mixed at concentrations of 1 and 2% in water, then emulsified. The citrus groves are sprayed at a rate of 1200 L/ha. The efficacy of these emulsions is compared to that of an emulsion of the prior art T1, as described hereinafter and to a chemical reference product corresponding to the use of a synthetic pesticide, here Chlorpyrifos, reference T2.

For the emulsion T1, the concentrate is prepared using 1.4% ethoxylated $C_{12}$-$C_{14}$ alcohol and 1.6% ethoxylated $C_{13}$ alcohol acid phosphate in the same mixture of hydrocarbons. As previously, this concentrate is mixed at concentrations of 1 and 2% in water then emulsified. The resulting emulsions are applied in an identical manner onto citrus.

The efficacy of these emulsions in preventing harmful insect activity is then evaluated, by comparison with the reference products and the prior art. To this end, a count is undertaken of the number of insects present at the time of application of the emulsions on the reference, and the number of insects having withstood the treatment after 20 days. The efficacy is measured according to the Abbott formula based on the number of live insects, the number of dead insects and the % of citrus infected (more than 3 insects per fruit).

The Abbott formula is the following:

% efficacy=[(untreated−treated)/untreated]×100

The results are given in Table III and IV below. (l/hl indicates l of concentrate per hl of water)

TABLE III

| | | Name of Parasite Aonidiella aurantii Type of Evaluation | | | | |
|---|---|---|---|---|---|---|
| | | Number of live individuals | Number of live individuals | Number of dead individuals Reference time | % mortality | % fruits infected |
| Treatment | Concentration | t = 0 | t + 20 days | t + 20 days | t + 20 days | t + 20 days |
| R | — | 225.5 | 231.8 | 3.0 | 1.3 | 46.5 |
| E4 | 1.0 l/hl | 215.3 | 58.0 | 145.0 | 71.4 | 12.3 |
| E4 | 2.0 l/hl | 211.0 | 22.0 | 175.5 | 88.8 | 7.8 |
| T1 | 1.0 l/hl | 216.8 | 59.0 | 160.0 | 73.0 | 12.3 |
| T1 | 2.0 l/hl | 207.3 | 21.5 | 177.5 | 89.1 | 7.0 |
| T2 | 0.15 l/hl | 216.5 | 23.5 | 172.0 | 88.0 | 7.8 |

TABLE IV

| | | Name of Parasite *Aonidiella aurantii* Type of Evaluation | |
|---|---|---|---|
| | | % Efficacy (Based on the number of live individuals) | % Efficacy (Based on mortality) |
| | | Reference time (days) | |
| Treatment | Concentration | t + 20 | t + 20 |
| E4 | 1.0 l/hl | 75.0 | 73.7 |
| E4 | 2.0 l/hl | 90.5 | 83.3 |
| T1 | 1.0 l/hl | 74.5 | 73.7 |
| T1 | 2.0 l/hl | 90.7 | 84.9 |
| T2 | 0.15 l/hl | 89.9 | 83.3 |

The invention claimed is:

1. An emulsifiable concentrate for an emulsified phytosanitary composition, comprising:
   more than 90% by weight of at least one mixture of hydrocarbons having a distillation cut greater than 250° C., comprising less than 20% by weight n-paraffins and less than 1% aromatics,
   from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 and the HLB of the mixture of which varies from 6 to 10, wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, the HLB of the TA1 varying from 5 to 16, and
   from 0.0001% to 1% by weight of water;
   wherein the hydrocarbon mixture comprises more than 50% by weight of hydrocarbons containing from 15 to 30 carbon atoms.

2. The concentrate according to claim 1, further comprising from 2 to 3% surfactant TA1, and from 0.1 to 0.9% surfactant TA2.

3. The concentrate according to claim 1, wherein the water content is comprised between 0.05 and 0.5% by weight of the concentrate.

4. The concentrate according to claim 1, wherein the surfactant TA1 is chosen from the polyethoxylated oleic acids comprising from 4 to 8 ethoxylated radicals.

5. The concentrate according to claim 1, wherein the surfactant TA2 is selected from the group consisting of:
   sorbitan mono- and/or polycarboxylates;
   ethoxylated sorbitan mono- and/or polycarboxylates;
   glycerol mono- and/or polycarboxylates; and
   ethoxylated glycerol mono- and/or polycarboxylates,
   each polycarboxylate group comprising 1 to 3 carbon chains of 12 to 20 carbon atoms having at least one olefin bond, the polyethoxylated group comprising 1 to 5 ethoxylated groups, the HLB of the TA2 varying from 1 to 11.

6. The concentrate according to claim 1, wherein the surfactant TA2 is a sorbitan monooleate or a glycerol monooleate or their mixture.

7. A phytosanitary emulsion comprising:
   a) from 0.5% by weight to 10% by weight of an emulsifiable concentrate comprising:
      i) more than 90% by weight of at least one mixture of hydrocarbons having a distillation cut greater than 250° C., comprising less than 20% by weight n-paraffins and less than 1% aromatics,
      ii) from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 and the HLB of the mixture of which varies from 6 to 10; wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, and HLB of the TA1 varying from 5 to 16, and
      iii) from 0.0001% to 1% by weight of water; and
   b) from 99.5% to 90% fresh and/or salt water;
   c) wherein the hydrocarbon mixture comprises more than 50% by weight of hydrocarbons containing from 15 to 30 carbon atoms.

8. The emulsion according to claim 7, comprising from 0.5 to 3% by weight of the concentrate and from 97 to 99.5% fresh and/or salt water, which emulsion has a creaming time according to the procedure MT36 between 25 seconds and 2 minutes.

9. The emulsion according to claim 7, wherein the emulsion does not show any deposit after 14 days of storage at 54° C. according to a procedure recommended by CIPAC MT 46.3.1.

10. A method for producing the emulsion according to claim 7, further comprising mixing the concentrate and the water in a tank on the site of application of the emulsion and emulsifying it by a static emulsifier or a rotor stator mixer.

11. A method for the insecticidal and/or fungicidal treatment of crops comprising the step of spraying onto crops a phytosanitary emulsion comprising:
   a. From 0.5% by weight to 10% by weight of an emulsifiable concentrate comprising:
      i. more than 90% by weight of at least one mixture of hydrocarbons having a distillation cut greater than 250° C., comprising less than 20% by weight n-paraffins and less than 1% aromatics,
      ii. from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 and the HLB of the mixture of which varies from 6 to 10, wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, the HLB of the TA1 varying from 5 to 16, and
      iii. from 0.0001% to 1% by weight of water; and
   b. from 99.5% to 90% fresh and/or salt water;
   c. wherein the hydrocarbon mixture comprises more than 50% by weight of hydrocarbons containing from 15 to 30 carbon atoms.

12. The method according to claim 11 wherein the phytosanitary emulsion is sprayed onto fruit tree crops.

13. The method according to claim 12, wherein the fruit tree crops comprise banana trees or lemon trees.

14. A homogeneous oil film obtained by vaporization of an emulsion comprising:
  a. from 0.5% by weight to 10% by weight of an emulsifiable concentrate comprising:
    i. more than 90% by weight of at least one mixture of hydrocarbons having a distillation cut greater than 250° C., comprising less than 20% by weight n-paraffins and less than 1% aromatics, and
    ii. from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 the HLB of the mixture of which varies from 6 to 10; wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, the HLB of the TA1 varying from 5 to 16, and
    iii. from 0.0001% to 1% by weight of water;
  b. from 99.5% to 90% fresh and/or salt water;
  c. the homogenous oil film being deposited on trunks and leaves, and comprising less than 5% water; and
  d. wherein the hydrocarbon mixture comprises more than 50% by weight of hydrocarbons containing from 15 to 30 carbon atoms.

15. An emulsifiable concentrate for an emulsified phytosanitary composition, comprising:
  more than 90% by weight of at least one mixture of hydrocarbons having a distillation cut greater than 250° C., comprising less than 20% by weight n-paraffins and less than 1% aromatics,
  from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 and the HLB of the mixture of which varies from 6 to 10, wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, the HLB of the TA1 varying from 5 to 16, and
  from 0.0001% to 1% by weight of water;
  wherein the mixture of hydrocarbons comprises less than 10 ppm sulphur and less than 100 ppm aromatics and is chosen from the group constituted by the hydrodewaxed hydrocarbons containing more than 50% by weight isoparaffins and desulphurized and dearomatized hydrocarbons containing more than 20% by weight naphthenes of which more than 10% are polynaphthenes.

16. The concentrate according to claim 15, wherein the composition does not show any deposit after 14 days of storage at 54° C. according to a procedure recommended by CIPAC MT 46.3.1.

17. An emulsifiable concentrate for an emulsified phytosanitary composition, comprising:
  more than 90% by weight of at least one mixture of hydrocarbons having a distillation cut greater than 250° C., comprising less than 20% by weight n-paraffins and less than 1% aromatics,
  from 1 to 4% by weight of a mixture of at least a first surfactant (TA1) and a second surfactant (TA2), such that TA2 is more hydrophobic than TA1 for a difference in hydrophile-lipophile balance (HLB) between TA1 and TA2 varying from 3 to 11 and the HLB of the mixture of which varies from 6 to 10, wherein the first surfactant TA1 is chosen from polyalkoxylated carboxylic acids, comprising a carbon chain with 16 to 20 carbon atoms having at least one olefin bond, each polyalkoxylated group comprising from 3 to 15 alkoxylated radicals, itself comprising from 1 to 4 carbons per oxygen atom, the HLB of the TA1 varying from 5 to 16, and
  from 0.0001% to 1% by weight of water;
  wherein the mixture of hydrocarbons is chosen from gas oil cuts having boiling points above 250° C., originating from hydrocracking vacuum distillate gas oils or other refining processes, these cuts having been desulphurized and/or dearomatized by catalytic hydrogenation then distilled into cuts with ranges of less than 75° C., these cuts comprising more than 20% naphthenes and having a pour point below −15° C.

18. The concentrate according to claim 17, wherein the hydrocarbon mixture comprises more than 50% by weight of hydrocarbons containing from 15 to 30 carbon atoms.

19. The concentrate according to claim 17, wherein the composition does not show any deposit after 14 days of storage at 54° C. according to a procedure recommended by CIPAC MT 46.3.1.

* * * * *